Jan. 2, 1973 M. C. VAN STAAVEREN Plant Pat. 3,284

HYBRID ALSTROEMERIA PLANT

Filed April 9, 1971 2 Sheets-Sheet 1

INVENTOR.
MAURITS C. VAN STAAVEREN

BY Rummler & Snow
Attys.

HYBRID ALSTROEMERIA PLANT

Filed April 9, 1971 2 Sheets-Sheet 2

United States Patent Office

Plant Pat. 3,284

Patented Jan. 2, 1973

3,284

HYBRID ALSTROEMERIA PLANT

Maurits C. van Staaveren, 30 Hornweg, Aalsmeer, Netherlands

Filed Apr. 9, 1971, Ser. No. 132,917
Int. Cl. A01h 5/00
U.S. Cl. Plt.—68 1 Claim

ABSTRACT OF THE DISCLOSURE

A new variety of hybrid alstroemeria plant characterized by the unusual pink color of its blooms, its vigorous growth and branching of the flower stalk, its tendency to flower the year around with an abundant flower crop on each stalk, and the long lasting quality of the blooms as a cut flower.

BACKGROUND OF THE INVENTION

This new variety of alstroemeria plant originated as a seedling produced by me at Aalsmeer, Holland, by my crossing *Alstroemeria aurantica* "Edison" (unpatented) with *Alstroemeria Pelegrina,* in 1964, with the object of developing commercially attractive plants having novel flower coloring and improved strength and growth habit. The new pink coloring of the blossoms of this new plant and its tendency to bloom profusely the year around led to its selection for propagation and trial and asexual reproduction of this new variety, under my direction at Aalsmeer, Holand, through many successive generations not only showed that the first observed color and blooming habits are fixed and hold true from generation to generation, but also that the new plant had a very vigorous growth habit resulting in a taller plant than either of its parents, producing more flower stalks per plant each year and much improved branching of each flower stalk, all of which characteristics also appear to be fixed and hold true through successive propagations which are done by dividing the rootstock.

DESCRIPTION OF THE DRAWINGS

My new variety of alstroemeria plant is illustrated by the accompanying drawings which show the color characteristics of the flowers as nearly true as it is reasonably possible to obtain by conventional photographic procedure and in which.

DESCRIPTION OF THE NEW PLANT

The following is a detailed description of my new variety of alstroemeria plant with color designations according to the R.H.S. Colour Chart of the Royal Horticultural Society of London, England, the observations having been made at Aalsmeer, Holland, in August 1970.

*The plant*

Origin: Seedling.

Parentage:

*Seed parent.*—*Alstroemeria aurantica* "Edison" (unpatented)

*Polen parent.*—*Alstroemeria Pelegrina* (unpatented)

Form: Herb. A tall flower stalk having an umbel of flower-bearing branches at its top.

Height: 1 to 1.5 meters, including 15 to 25 cm. upright branches.

Growth: Upright and vigorous from a bud borne by the rootstock.

Rootstock: Tuberous. The rootstock tubers grow about 5 cm. per year, radiating in all directions, and each bears 35 to 50 buds, during the course of a year, producing a like number of flower stalks in various stages of development during the year.

Figure 1:
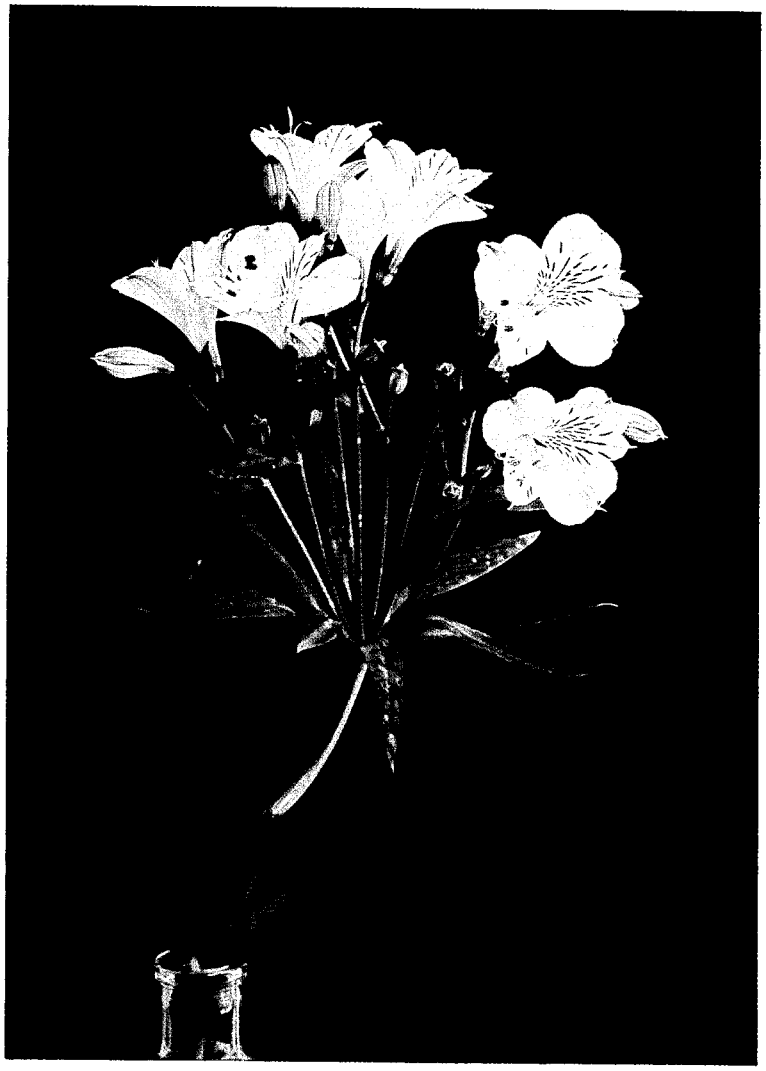
FIG. 1 is a view showing the branching upper portion of a typical flower stalk of the new plant in full bloom.

Branching: At top of flower stalk, 1 to 1.25 meters high, the stalk produces an umbel of 5 to 8 upright flower-bearing branches, each branch reaching a length of 15 to 25 cm. and bearing 3 to 5 buds. See FIG. 1.

Foliage—leaves:

*Quantity.*—20 to 30 leaves on each stalk. At each umbel there is a circle of leaves, one at each branch.

*Shape of leaf.*—Long and narrow—generally ensiform with entire margin. Leaves curl at about 1.5 cm. from stem to turn morphological underside upward.

*Size of leaf.*—8 to 11 cm. long x 2.0 cm. wide

*Texture.*—Soft.

*Appearance.*—Shiny.

*Color.*—Upper side—Yellow-Green 146A. Under side—Greyed-Green 191A.

*The bud*

Form: Young bud, 12 days before opening, is generally pear-shaped (#5 in FIG. 2). Mature bud, 1 to 2 days before opening, has shape of a long-necked pear (#6 in FIG. 2).

Size:

*Young bud.*—1.5 cm. long x 0.8 cm. in largest diameter.

*Mature bud.*—3.5 cm. long x 1.4 cm. in diameter.

Color: Mainly Yellow-Green 145B at top end and a glow of Red-Purple 62A at the base portion.

*The flower*

Blooming habit: Substantially continuous from January through November under Dutch climatological conditions. The first flower of each branch opens at the same time and the remaining flowers on each branch open successively about 4 days apart.

Figure 3:
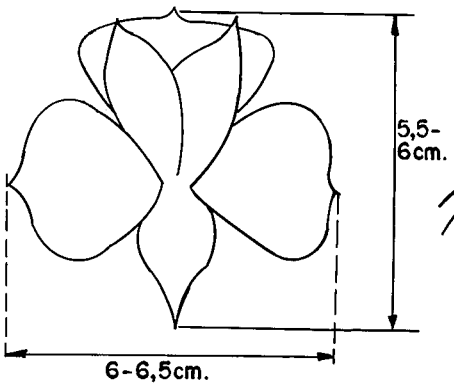
FIG. 3 is a sketch showing the face or front view arrangement of the flower petals.
Figure 4:
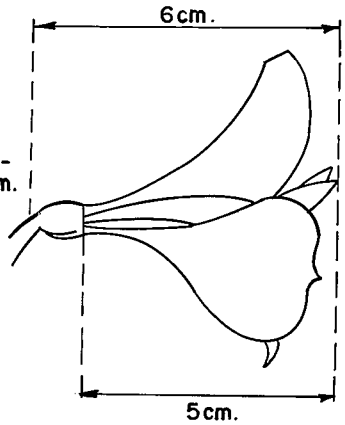
FIG. 4 is a sketch showing the side view arrangement of the flower petals.

Size: Large—6 cm. long x 6 to 6.5 cm. diameter spread of petals. See FIGS. 3 and 4.

Borne: Singly on peduncle of medium length. 3 to 5 buds on each branch bloom successively, one after the other, at about 4 day intervals.

Shape: Generally funnel-like.

Petalage: Number of petals—6.

*Arrangement.*—Two concentric circles of 3 petals each with alternating disposition.

Figure 2:
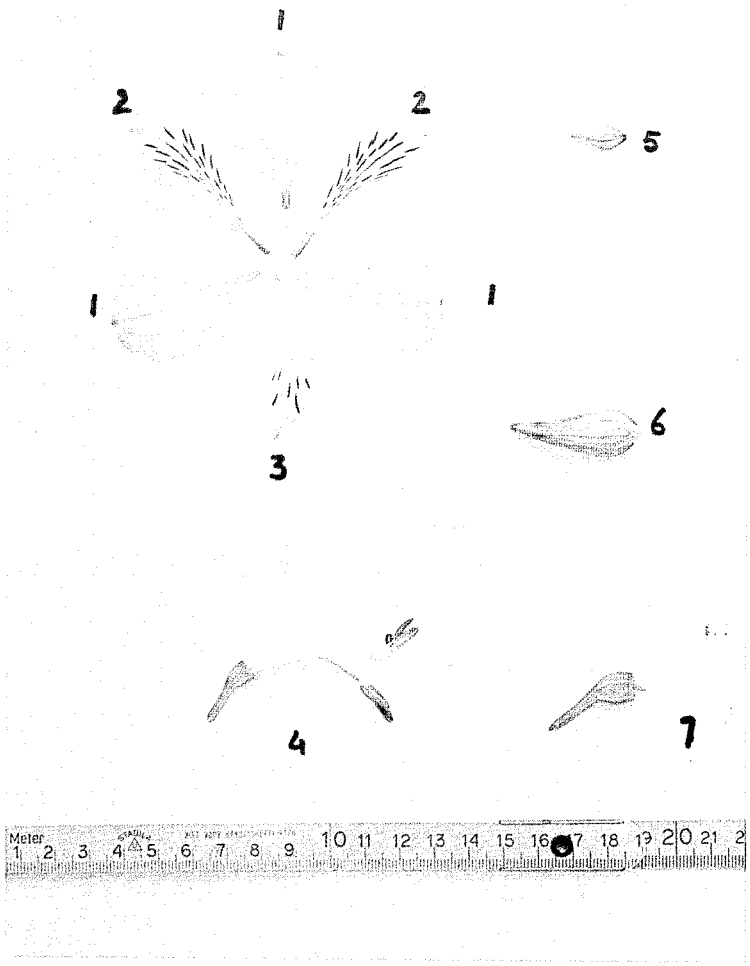
FIG. 2 shows the petals and reproductive organs, of a typical flower, young and mature buds, and a specimen of the fruit.

*Form.*—Outer petals, #1 in FIG. 2, generally spatulate with broad blade and eneire margin. Inner petals—upper pair—#2 in FIG. 2, oblanceolate with broad blade, entire margin, and mucronate tip; lower petal—#3 in FIG. 2, oblanceolate with narrow blade, entire margin, and cuspidate tip.

*Color.*—Outer petals—inside surface, Red-Purple 62C with tips of Red-Purple 62B. Outside surface, Red-Purple 62D crossed by veins of Green 141C. Inner petals—Nectary bearing, #2 in FIG. 2, Yellow 12A in central area, yellow 12D at base, and Red-Purple 62B at tip end. Inner petals—bottom petal, #3 in FIG. 2, Red-Purple 62B at tip end, Yellow 12D over balance of petal area. All three of the inner petals have long central and short lateral stripes of Greyed-Purple 187 color ranging through 187A, B and C and depending on size of stripe, the largest being of 187A, the smallest of 187C and all stripes are crossed by veins of Green 141C color.

*Texture.*—Soft.

*Appearance.*—Shiny.

Effect of weather: Color, texture and appearance are not affected by hot or wet weather.

Lasting quality.—On plant—7 to 9 days for each flower. As cut flower—7 days for each flower.

*Reproductive organs*

Stamens (#4 in FIG. 2):

*Anthers.*—Number—6. Length—0.8 cm. Arrangement—One opposite each petal. Color—Yellow-Green 148D.

*Filaments.*—Length—4.45 cm. Color—Red-Purple 73D.

Pollen: Color—Yellow-Green 147A.

Pistil: Number—1. Length 4–4.5 cm.

Stigmas: Number—3. Color—Orange-Red 35C.

*The fruit*

Generally round in shape with rather flat end bearing a centrally-located short and pointed protrusion (#7 in FIG. 2). The fruit is of capsular form with 3 compartments each containing 2 rows of ovaries attached to the central standing placenta. No seeds are produced and the plant is sterile.

My new variety of alstroemeria plant is distinguished from its seed parent *Alstroemeria aurantica* "Edison" by its more abundant flower crop, greater number of flower stalks per plant, better branching of the flower stalk and more flowers per branch. Also, the new variety has the tendency to flower the year around, whereas "Edison" flowers only in the summertime, and the color of the new variety is Pink, whereas the color of "Edison" is Yellow.

Compared with its pollen-parent, *Alstroemeria Pelegrina,* the new variety has a tall growing habit with unusually long flower stalks, whereas the flower stalks of the pollen parent are only of moderate length.

I claim:

1. The new and distinct variety of alstroemeria plant substantially as herein shown and described, characterized by the pink color of its flowers, the abundance of flower stalks and blooms produced by each plant, its tendency to bloom the year around, and the very long lasting quality of the flowering portion of the plant as a cut flower.

No references cited.

ROBERT E. BAGWILL, Primary Examiner